United States Patent
Tsukamoto et al.

(10) Patent No.: US 7,491,840 B2
(45) Date of Patent: Feb. 17, 2009

(54) COMPOUND AND COMPOSITION CONTAINING THE SAME

(75) Inventors: Kazuya Tsukamoto, Sodegaura (JP); Nobumasa Arashiba, Tokyo (JP); Akinori Nagatomo, Omuta (JP); Kouki Oogaki, Omuta (JP); Takeshi Kobayashi, Omuta (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 11/360,501

(22) Filed: Feb. 24, 2006

(65) Prior Publication Data

US 2006/0205971 A1    Sep. 14, 2006

Related U.S. Application Data

(63) Continuation of application No. PCT/JP2005/003899, filed on Mar. 7, 2005.

(60) Provisional application No. 60/659,396, filed on Mar. 8, 2005.

(30) Foreign Application Priority Data

Mar. 12, 2004    (JP) .............................. 2004-070791

(51) Int. Cl.
C07C 69/00 (2006.01)
(52) U.S. Cl. ..................................... 560/144
(58) Field of Classification Search ........................ None
See application file for complete search history.

(56) References Cited

U.S. PATENT DOCUMENTS 4,446,216 A * 5/1984 Smith et al. .................. 430/405

FOREIGN PATENT DOCUMENTS

| | | | |
|---|---|---|---|
| EP | 0 351 832 A2 | | 1/1990 |
| EP | 1 724 302 A1 | | 11/2006 |
| EP | 1 820 667 A1 | | 8/2007 |
| FR | 2084347 | * | 12/1971 |
| JP | 58-108527 A | | 6/1983 |
| JP | 63-284291 A | | 11/1988 |
| JP | 07-118621 | | 5/1995 |
| JP | 52-90307 A | | 7/1997 |
| JP | 2001-234140 | | 8/2001 |

OTHER PUBLICATIONS

Jin et al., "Main Chain Thermotropic Polyesters Having Flexible Spacers—Influence of Ester Group Linking Order Between Mesogenic Unit and Flexible Spacer," *Journal of Polymer Science, Part B: Polymer Physics*, Mar. 1990, pp. 531-543, vol. 28, No. 4, John Wiley & Sons, Inc.
XP 002467730, Database Accession No. 2542492, Abstract.
XP 002467731, Database Accession No. 2307363, Abstract.

* cited by examiner

*Primary Examiner*—Paul A Zucker
(74) *Attorney, Agent, or Firm*—Buchanan Ingersoll & Rooney PC

(57) ABSTRACT

This invention provides a compound represented by the following general formula (1) and capable of suppressing the blooming, which is observed in the compounding of the resorcin or the RF resin, as far as possible while maintaining the workability and high humidity-aged adhesion of the rubber composition obtained by compounding with rubber, reducing the deterioration of the adhesiveness during the storage of the rubber composition and stably developing the adhesiveness as well as the composition containing the above-mentioned compound as a main component:

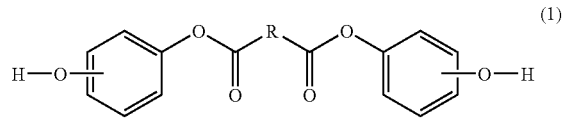

(1)

(wherein R represents a divalent aliphatic group having a carbon number of 1-16).

6 Claims, No Drawings

COMPOUND AND COMPOSITION CONTAINING THE SAME

TECHNICAL FIELD

This invention relates to a novel composition or compound improving an adhesion durability to a metal reinforcing material such as a steel cord used for rubber products such as a pneumatic tire, an industrial belt and the like. More particularly, this invention relates to a compound having a specific structure capable of improving a workability of a rubber composition obtained by compounding with rubber and of stably developing an initial adhesion and a humidity-aged adhesion to a metal reinforcing material regardless of the storage period of the rubber composition, as well as a composition mainly containing the above-mentioned compound.

BACKGROUND ART

In the rubber products particularly requiring the strength such as tires for automobiles, conveyor belts, hoses and the like, a composite material formed by covering a metal reinforcing material such as a steel cord with a rubber composition is used for the purpose of reinforcing rubber to improve the strength and durability. In order that the rubber-metal composite material develops a high reinforcing effect to provide a reliability, a stable adhesiveness not depending on conditions of mixing, compounding, storage and so on is required between the rubber and the metal reinforcing material. In order to obtain such a composite material, there is widely used a so-called direct vulcanization adhesion, in which the metal reinforcing materials such as steel cords or the like plated with zinc, brass or the like are embedded in the rubber composition containing sulfur and adhered thereto at the same time as the vulcanization of rubber during the vulcanization by heating. Until now, there are made various investigations for improving the adhesiveness, particularly the humidity-aged adhesion between the rubber and the metal reinforcing material in the direct vulcanization adhesion.

For example, there is reported a rubber composition in which a resorcin or a resorcin-formaldehyde resin (hereinafter abbreviated as "RF resin") obtained by the condensation of resorcin and formalin is compounded for improving the humidity-aged adhesion (see JP-A-2001-234140). The humidity-aged adhesion between the steel cord and the rubber is certainly improved by compounding the RF resin.

However, the resorcin or the RF resin is poor in the compatibility with rubber because the polarity is very high, and the precipitation of the resorcin or the RF resin or so-called blooming is caused in accordance with conditions of mixing, compounding, storage and so on, so that there is a fear of damaging an appearance of the rubber product. And also, when the rubber composition is stored over a long time of period ranging from the compounding to the vulcanization adhesion, a problem of deteriorating the adhesiveness is caused by blooming, so that it is necessary to rapidly conduct the vulcanization adhesion of the rubber composition containing the resorcin or the RF resin, which may detract the productivity of the rubber product.

Also, an adhesive material made from a mixed polyester having a resorcin skeleton with a weight average molecular weight of 3000-45000 is reported (see JP-A-7-118621). Although the mixed polyester having a high molecular weight is more compatible with the rubber as compared with the RF resin, the compatibility can not still be satisfied. Moreover, when the mixed polyester having a high molecular weight is compounded with rubber, the viscosity of the compounded rubber is increased to cause a problem of lowering the workability, and the humidity-aged adhesion is not sufficient.

SUMMARY OF THE INVENTION

It is, therefore, an object of the invention to provide a compound having a specific structure capable of suppressing the blooming, which was seen in the compounding of the resorcin or the RF resin, as far as possible while maintaining the workability and high humidity-aged adhesion of the rubber composition at the time of compounding with rubber, and reducing the deterioration of the adhesiveness during the storage of the rubber composition, and developing an excellent adhesion stability, as well as a composition containing the above-mentioned compound as a main component.

The inventors have made various studies in order to achieve the above object, and found that when the compound having a specific structure or the composition containing the compound as a main component is compounded with rubber, the workability of the rubber composition, which is a problem in the compounding of the resorcin or RF resin with rubber, can be improved while maintaining the humidity-aged adhesion equal to or more than that of the resorcin or RF resin containing system to suppress the occurrence of the blooming and an excellent adhesion stability can be attained without depending on the conditions of compounding, storage and so on, and as a result the invention has been accomplished.

That is, the invention is concerned with (I) a compound represented by the following general formula (1)

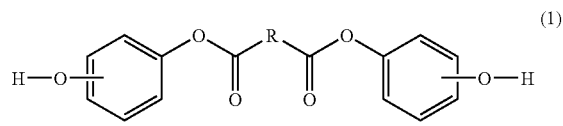

(wherein R is a divalent aliphatic group having a carbon number of 1-16);

(II) a compound according to the item (I), wherein the compound represented by the general formula (1) is a compound represented by the following general formula (2)

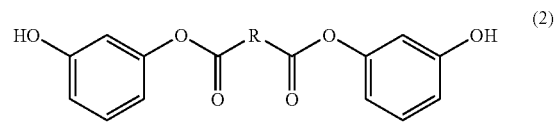

(wherein R is a divalent aliphatic group having a carbon number of 1-16); and (III) a composition comprising 60-100 wt % of the compound represented by the general formula (2), 0-20 wt % of a compound represented by the following general formula (3) in which n is 2, 0-10 wt % of a compound represented by the following general formula (3) in which n is 3 and 0-10 wt % of a compound represented by the following general formula (3) in which n is 4-6, provided that the composition does not include a pure material consisting of 100 wt % of the compound represented by the general formula (2):

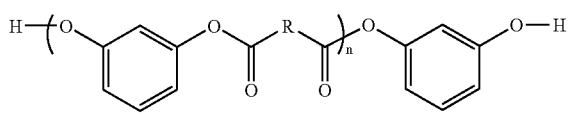

(wherein R is a divalent aliphatic group having a carbon number of 1-16, and n is an integer of 2-6).

According to the invention, there can be provided compounds capable of suppressing the blooming, which is observed in the compounding of the resorcin or the RF resin, as far as possible while maintaining the workability and high humidity-aged adhesion of the rubber composition obtained by compounding with rubber, reducing the deterioration of the adhesiveness during the storage of the rubber composition and stably developing the adhesiveness as well as the composition containing the above-mentioned compound as a main component.

BEST MODE FOR CARRYING OUT THE INVENTION

The invention will be described in detail below. The compound of the invention is represented by the general formula (1). R in the general formula (1) is a divalent aliphatic group having a carbon number of 1-16. As the compound represented by the general formula (1) are mentioned, for example, compounds represented by the general formula (2). R in the general formula (2) is the same meaning as R in the general formula (1).

As the divalent aliphatic group having a carbon number of 1-16 are mentioned, for example, linear or branched alkylene groups such as methylene group, ethylene group, butylene group, isobutylene group, octylene group, 2-ethylhexylene group and the like; linear or branched alkenylene groups such as vinylene group (ethenylene group), butenylene group, octenylene group and the like; a substituted alkylene group or a substituted alkenylene group in which hydrogen atom in the above-mentioned alkylene or alkenylene group is substituted with hydroxyl group, amino group or the like; and a cycloaliphatic group such as cyclohexylene group or the like. Among them, an alkylene group having a carbon number of 2-10 is preferable for reasons of availability, and ethylene group, butylene group and octylene group are particularly preferable.

As a concrete example of the compound represented by the general formula (1) are mentioned bis(2-hydroxyphenyl)malonate, bis(2-hydroxyphenyl)succinate, bis(2-hydroxyphenyl)fumarate, bis(2-hydroxyphenyl)maleate, bis(2-hydroxyphenyl)malate, bis(2-hydroxyphenyl)itaconate, bis(2-hydroxyphenyl)citraconate, bis(2-hydroxyphenyl)adipate, bis(2-hydroxyphenyl)tartrate, bis(2-hydroxyphenyl)azelate, bis(2-hydroxyphenyl)sebacate, bis(2-hydroxyphenyl)cyclohexanedicarboxylate, bis(3-hydroxyphenyl)malonate, bis(3-hydroxyphenyl)succinate, bis(3-hydroxyphenyl)fumarate, bis(3-hydroxyphenyl)maleate, bis(3-hydroxyphenyl)malate, bis(3-hydroxyphenyl)itaconate, bis(3-hydroxyphenyl)citraconate, bis(3-hydroxyphenyl)adipate, bis(3-hydroxyphenyl)tartrate, bis(3-hydroxyphenyl)azelate, is(3-hydroxyphenyl)sebacate, bis(3-hydroxyphenyl)cyclohexanedicarboxylate, bis(4-hydroxyphenyl)malonate, bis(4-hydroxyphenyl)succinate, bis(4-hydroxyphenyl)fumarate, bis(4-hydroxyphenyl)maleate, bis(4-hydroxyphenyl)itaconate, bis(4-hydroxyphenyl)citraconate, bis(4-hydroxyphenyl)adipate, bis(4-hydroxyphenyl)tartrate, bis(4-hydroxyphenyl)azelate, bis(4-hydroxyphenyl)sebacate, bis(4-hydroxyphenyl)cyclohexanedicarboxylate and the like.

Among them, bis(3-hydroxyphenyl)malonate, bis(3-hydroxyphenyl)succinate, bis(3-hydroxyphenyl)fumarate, bis(3-hydroxyphenyl)maleate, bis(3-hydroxyphenyl)malate, bis(3-hydroxyphenyl)itaconate, bis(3-hydroxyphenyl)citraconate; bis(3-hydroxyphenyl)adipate, bis(3-hydroxyphenyl)tartrate, bis(3-hydroxyphenyl)azelate, bis(3-hydroxyphenyl)sebacate and bis(3-hydroxyphenyl)cyclohexanedicarboxylate are preferable, and bis(3-hydroxyphenyl)succinate, bis(3-hydroxyphenyl)adipate and bis(3-hydroxyphenyl)sebacate are particularly preferable.

The production method of the compound represented by the general formula (1) is not particularly limited, but is produced, for example, by reacting a dicarboxylic acid halide represented by the following general formula (4):

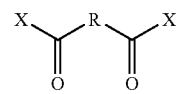

(wherein R is a divalent aliphatic group having a carbon number of 1-16, and X is a halogen atom) with a compound represented by the following general formula (5):

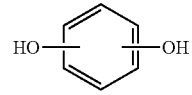

in the presence or absence of a base.

In the general formula (4), R is the same meaning as R in the general formula (1), and X is a halogen atom. As the halogen atom, a chlorine atom and a bromine atom are preferable.

As the compound represented by the general formula (4) are mentioned aliphatic dicarboxylic acid dichlorides such as malonyl dichloride, succinyl dichloride, fumaroyl dichloride, maleoyl dichloride, glutaryl dichloride, adipoyl dichloride, suberoyl dichloride, azelaoyl dichloride, sebacoyl dichloride, 1,10-decanedicarbonyl dichloride, 1,12-dodecanedicarbonyl dichloride, 1,16-hexadecanedicarbonyl dichloride and the like; cycloaliphatic dicarboxylic acid dichlorides such as cyclohexanedicarbonyl dichloride, cyclohexenedicarbonyl dichloride and the like; aliphatic dicarboxylic acid dibromides such as malonyl dibromide, succinyl dibromide, fumaroyl dibromide, maleoyl dibromide, glutaryl dibromide, adipoyl dibromide, suberoyl dibromide, azelaoyl dibromide, sebacoyl dibromide, 1,10-decanedicarbonyl dibromide, 1,12-dodecanedicarbonyl dibromide, 1,16-hexadecanedicarbonyl dibromide and the like; and cycloaliphatic dicarboxylic acid dibromides such as cyclohexanedicarbonyl dibromide, cyclohexenedicarbonyl dibromide and the like. Among them, malonyl dichloride, succinyl dichloride, adipoyl dichloride, azelaoyl dichloride, sebacoyl dichloride, malonyl dibromide, succinyl dibromide, adipoyl dibromide, azelaoyl dibromide and sebacoyl dibromide are preferable.

On the other hand, as the compound represented by the general formula (5) are mentioned catechol, resorcin and hydroquinone.

As the base used in the reaction of the compound represented by the general formula (4) with the compound represented by the general formula (5) are usually used organic bases such as pyridine, β-picoline, N-methylmorpholine, dimethylaniline, diethylaniline, trimethylamine, triethylamine, tributylamine and the like.

When the compound represented by the general formula (4) is reacted with the compound represented by the general formula (5), a molar ratio of the compound represented by the general formula (4) to the compound represented by the general formula (5) is usually 1:4-1:30.

When the compound represented by the general formula (4) is reacted with the compound represented by the general formula (5), a solvent may be used for the purpose of dissolving the starting materials. As the solvent may be used the above-mentioned organic bases as it is and other organic solvents not obstructing the reaction. As the latter solvent is mentioned ether such as dimethyl ether, dioxane or the like.

When the compound represented by the general formula (4) is reacted with the compound represented by the general formula (5), the reaction temperature is usually $-20°$ C.-$100°$ C.

The compound represented by the general formula (1) and obtained from the above-mentioned reaction can be isolated from the reaction mixture by a well-known method. There are mentioned a method in which the organic base and the compound represented by the general formula (5) used for the reaction and further an organic solvent if it is used for the reaction are evaporated and dried by an operation of a vacuum distillation or the like, a method in which a poor solvent for the compound represented by the general formula (1) is added to the reaction mixture to conduct re-precipitation, a method in which a water and a water immiscible organic solvent are added to the reaction mixture to extract into an organic phase, and so on. Moreover, in some cases, it may be purified by recrystallization.

As the poor solvent for the compound represented by the general formula (1) is usually used a water. Moreover, as the water immiscible organic solvent are used esters such as ethyl acetate, butyl acetate and the like; and ketones such as methyl isobutyl ketone, diisobutyl ketone and the like.

When resorcin is used as the compound represented by the general formula (5), a composition composed mainly of the compound represented by the general formula (2) and comprising the compound represented by the general formula (2) and the compound represented by the general formula (3) can be obtained.

R in the general formula (3) is the same meaning as R in the general formula (1), and n is an integer of 2-6.

For example, the composition obtained by using resorcin in the above-mentioned reaction and comprises the compound represented by the general formula (2) and the compound represented by the general formula (3) usually includes 60-100 wt % of the compound represented by the general formula (2), 0-20 wt % of the compound represented by the general formula (3) wherein n is 2, 0-10 wt % of the compound represented by the general formula (3) wherein n is 3, and about 10 wt % in total of the compounds represented by the general formula (3) wherein n is 4-6. The ratio of these compounds can be controlled by adjusting a molar ratio of the compound represented by the general formula (4) to resorcin.

The composition comprising the compound represented by the general formula (2) and the compound represented by the general formula (3) can be also isolated from the reaction mixture containing them in the same manner as in the isolation method of the compound represented by the general formula (1).

In case of the composition containing not less than 60 wt % of the compound represented by the general formula (2), the humidity-aged adhesion when being compounded with rubber and adhered is improved. In view of the improvement of the humidity-aged adhesion, the content of the compound represented by the general formula (2) is more preferably 70-100 wt %, further preferably 80-100 wt %.

The compound according to the invention and the composition containing such a compound as a main component have a characteristic of easily mixing with a rubber component as compared with resorcin or the RF resin. Therefore, the rubber composition comprising the compound according to the invention and the composition containing such a compound as a main component tends to hardly cause the blooming as compared with the rubber composition comprising resorcin or the RF resin. This is presumed due to the fact that the compound according to the invention and the composition containing such a compound as a main component are low in the polarity as compared with resorcin and the RF resin. Furthermore, the rubber composition comprising the compound according to the invention and the composition containing such a compound as a main component is excellent in the adhesion stability irrespectively of the storage period. Therefore, the compound according to the invention and the composition containing such a compound as a main component are useful as an adhesion improver.

EXAMPLE

The invention will be described in detail with reference to the following examples, referential examples and comparative examples, but the invention is not limited to these examples.

Example 1

A solution of 330.6 g (3.0 mol) of resorcin in 600.0 g of pyridine is kept below $15°$ C. on an ice bath, and 54.9 g (0.30 mol) of adipoyl chloride is gradually dropped into the solution. After the dropping, the temperature of the resulting reaction mixture is raised to room temperature and left to stand over a whole day and night to complete the reaction. From the reaction mixture is distilled off pyridine under a reduced pressure, and the resulting residue is added with 1200 g of water and cooled on ice to precipitate a deposit. The precipitated deposit is filtered and washed with water, and the thus obtained wet body is dried under vacuum to obtain 84 g of a white-light yellow powder. The powder is treated by a liquid chromatography provided with a preparative unit under the following conditions to batch off an elute containing a primary component. A crystal precipitated by the concentration of the elute is recovered by filtration and dried under vacuum to obtain a crystal having a melting point of 140-$143°$ C. As a result of a HPLC analysis, this crystal is bis(3-hydroxyphenyl)adipate having a purity of 98%.

The conditions of the preparative HPLC are shown as follows:

Column: Shim-pack PREP-ODS (made by SHIMADZU Corporation)

Column temperature: $25°$ C.

Eluting solution: methanol/water mixed medium (85/15 (w/w %))

Flow rate of eluting solution: 3 ml/min

Detector: UV detector (254 nm).

Moreover, the identification data of bis(3-hydroxyphenyl) adipate are shown as follows:
Datum of MS Spectrum
EI(Pos.) m/z=330
Data of IR Spectrum
3436 cm-1: hydroxyl group
2936 cm-1: alkyl
1739 cm-1: ester
Data of NMR spectra are shown in Table 1-1 and Table 1-2.

| TABLE 1-1 | | TABLE 1-2 | | | |
|---|---|---|---|---|---|
| C-NMR | | H-NMR | | | |
| Symbol | Measured Value (ppm) | Symbol | Measured Value (ppm) | Attribution | Proton Ratio |
| ① | 23.7 | a | 1.7 | —CH2— | 2 |
| ② | 33.1 | b | 2.6 | —CH2— | 2 |
| ③ | 109 | c | 6.4-6.7 | =CH | 3 |
| ④ | 112.1 | d | 7.2 | =CH | 1 |
| | 112.8 | e | 9.7 | —OH | 1 |
| ⑤ | 129.8 | | | | |
| ⑥ | 151.4 | | | | |
| ⑦ | 158.2 | | | | |
| ⑧ | 171.5 | | | | |

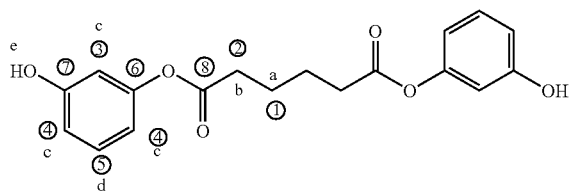

Example 2

As a result of HPLC analysis on 84 g of a powder obtained by conducting the same reaction as in Example 1, a content of bis(3-hydroxyphenyl)adipate in the powder is 89 wt %. The powder further contains 7 wt % of a compound of n=2 in a compound represented by the following formula (6) (hereinafter may be referred to as an oligomer), 2 wt % of a compound of n=3 in the compound represented by the formula (6), and 2 wt % of resorcin as a starting material. The compound represented by the formula (6) is identified by LC-MS.

(6)

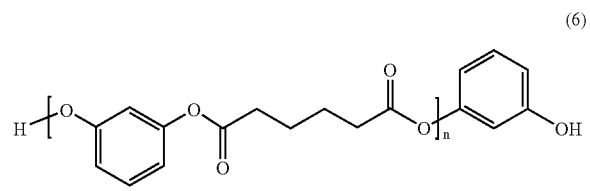

The measurement conditions of the MS spectrum are shown as follows:
Range of mass: 200-2000 amu (1.98+0.02 sec)
Ionization method: ESI (Electrospray)
Mode: positive
Capillary: 3.15 kV
Cone: 35V
S. B. Tmp.: 150° C.
Deslv. tmp.: 400° C.
Multi: 650 V N2: 750 L/hr
n=2: 551.1 [M+H]+, 568.2 [M+NH4]+
n=3: 771.2 [M+H]+, 788.2 [M+NH4]+
n=4: 1008.3 [M+NH4]+
n=5: 1228.3 [M+NH4]+

The analytical conditions of the HPLC are shown as follows:
1. Analysis of bis(3-hydroxyphenyl)adipate and resorcin
   Column: A-312 ODS from YMC Company
   Column temperature: 40° C.
   Eluting solution: methanol/water=7/3 (pH is adjusted to 3 with phosphoric acid)
   Detection: UV (254 nm).
2. Analysis of the oligomer
   Column: A-312 ODS from YMC Company
   Column temperature: 40° C.
   Eluting solution: acetonitrile/water=8/2 (pH is adjusted to 3.5 with acetic acid)
   Detection: UV (254 nm).

Example 3

The same procedure as in Example 1 is repeated except that the amount of resorcin is 176.2 g (1.6 mol), the amount of pyridine is 400 g and the amount of adipoyl chloride is 73.2 g (0.40 mol) to obtain 118.6 g of powder. As a result of the HPLC analysis, the powder contains 73.4 wt % of bis(3-hydroxyphenyl)adipate, 13.9 wt % of the compound of n=2 represented by the formula (6), 3.0 wt % of the compound of n=3 represented by the formula (6), 0.8 wt % of the compound of n=4 represented by the formula (6), 0.2 wt % of the compound of n=5 represented by the formula (6) and 2.9 wt % of resorcin as a starting material.

Example 4

A solution of 440.4 g (4.0 mol) of resorcin in 405.0 g of pyridine is kept below 15° C. on an ice bath, and 62.0 g (0.4 mol) of succinyl dichloride is gradually dropped into the solution. After the dropping, the temperature of the resulting reaction mixture is raised to room temperature and left to stand over a whole day and night to complete the reaction. From the reaction mixture is distilled off pyridine under vacuum, and the resulting residue is added with 1800 g of water and cooled on ice, during which the liquid becomes clouded wholly and separates into two phases. The extraction is carried out by adding 200 g of water and 600 g of ethyl acetate to an oil phase. The resulting organic phase is washed five times with cold water and then dried with magnesium sulfate. Thereafter, ethyl acetate is distilled off to obtain a viscous body, which is crystallized by adding 500 g of toluene, filtered, washed with toluene and then subjected to sludging twice with 1 L of water. The resulting wet body is dissolved into 100 g of methanol, re-precipitated by adding 1 L of water, filtered, washed and dried to obtain 82.3 g of light yellow powder. As a result of the HPLC analysis, a primary component of the powder is found to be a component having 91.0 area %. Also, the powder contains 0.7 wt % of resorcin. As a result of structural analysis, the primary component of the powder is found to be bis(3-hydroxyphenyl)succinate.

Moreover, identification data of bis(3-hydroxyphenyl)succinate are shown as follows:

Datum of MS Spectrum
  EI(Pos.) m/z=302
Data of IR Spectrum
  3361 cm-1: hydroxyl group
  2984 cm-1: alkyl
  1732 cm-1: ester
Data of NMR spectra are shown in Table 2-1 and Table 2-2.

| TABLE 2-1 | | TABLE 2-2 | | | |
|---|---|---|---|---|---|
| C-NMR | | H-NMR | | | |
| Symbol | Measured Value (ppm) | Symbol | Measured Value (ppm) | Attribution | Proton Ratio |
| ① | 30.1 | a | 3 | —CH2CH2— | 4 |
| ② | 109.9 | b | 6.5-6.7 | =CH | 6 |
| ③ | 113.5 | c | 7.2 | =CH | 2 |
|  | 114 |  |  |  |  |
| ④ | 130.8 |  |  |  |  |
| ⑤ | 153.1 |  |  |  |  |
| ⑥ | 159.6 |  |  |  |  |
| ⑦ | 172.7 |  |  |  |  |

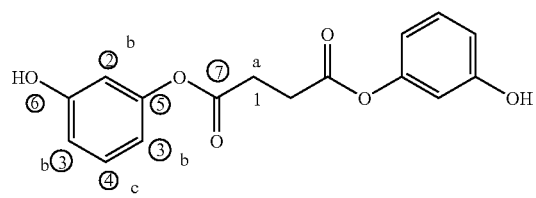

Example 5

A solution of 330.3 g (3.0 mol) of resorcin in 303.7 g of pyridine is kept below 15° C. on an ice bath, and 71.7 g (0.3 mol) of sebacoyl dichloride is gradually dropped into the solution. After the dropping, the temperature of the resulting reaction mixture is raised to room temperature and left to stand over a whole day and night to complete the reaction. From the reaction mixture is distilled off pyridine under vacuum, and the resulting residue is added with 250 g of water and cooled on ice to precipitate a deposit. The precipitated deposit is filtered and washed with water, and the resulting wet body is dried under vacuum to obtain 102.8 g of a whitelight yellow powder. As a result of the HPLC analysis, a primary component of the powder is found to be a component having 98.7 area %. Also, the powder contains 0.2 wt % of resorcin. As a result of structural analysis, the primary component of the powder is found to be bis(3-hydroxyphenyl) sebacate.

Moreover, identification data of bis(3-hydroxyphenyl)sebacate are shown as follows:

Datum of MS Spectrum
  EI(Pos.) m/z=386
Data of IR Spectrum
  3380 cm-1: hydroxyl group
  3000-2800 cm-1: long chain alkyl
  1732, 1749 cm-1: ester Data of NMR spectra are shown in Table 3-1 and Table 3-2.

| TABLE 3-1 | | TABLE 3-2 | | | |
|---|---|---|---|---|---|
| C-NMR | | H-NMR | | | |
| Symbol | Measured Value (ppm) | Symbol | Measured Value (ppm) | Attribution | Proton Ratio |
| ① | 26 | a | 1.4 | —CH2— | 8 |
| ② | 30.1 | b | 1.7 | —CH2— | 4 |
|  | 30.2 | c | 2.6 | —CH2— | 4 |
| ③ | 34.96 | d | 6.4-6.7 | =CH | 6 |
|  | 34.05 | e | 7.2 | =CH | 2 |
| ④ | 110 |  |  |  |  |
| ⑤ | 113.5 |  |  |  |  |
|  | 113.8 |  |  |  |  |
| ⑥ | 130.8 |  |  |  |  |
| ⑦ | 153.2 |  |  |  |  |
| ⑧ | 159.6 |  |  |  |  |
| ⑨ | 174 |  |  |  |  |

Reference Examples 1-5

Each of the compositions produced in Examples 1-5 is used as a test compound and mixed and milled with rubber according to a compounding recipe shown in Table 4 to prepare an unvulcanized rubber composition, and then the resistance to blooming, Mooney viscosity, adhesiveness just after the compounding and adhesiveness after the leaving of compounded rubber are measured and evaluated. The results are shown in Table 4.

(Resistance to Blooming)

After the unvulcanized rubber composition is stocked at 40° C. for 7 days, it is visually observed whether the compounding ingredient is separated out on the surface of rubber, which is judged by ○, Δ and x.

○: The compounding ingredient is not separated out on the surface.

Δ: The compounding ingredient is partially separated out on the surface.

x: The compounding ingredient is separated out on the whole surface.

(Mooney Viscosity)

ML(1+4)130° C. of the unvulcanized rubber composition is measured according to JIS K6300-2001. The smaller the numerical value, the better the result.

(Adhesion Test)

Steel cords (1×5 structure, wire diameter: 0.25 mm) plated with brass (Cu: 63 mass %, Zn: 37 mass %) are arranged in parallel to each other at an interval of 12.5 mm and coated with each of the rubber compositions from both sides thereof and immediately vulcanized at 160° C. for 15 minutes to prepare a sample having a width of 12.5 mm. After the steel cord is pulled out from the sample according to ASTM-D-2229 for the following adhesiveness, the rubber coated state is visually observed and represented by a value of 0-100% as an indicator of the adhesiveness. The larger the value, the better the property. The initial adhesion is measured just after the vulcanization. The humidity-aged adhesion is measured by aging at 70° C. and a humidity of 100% RH for 4 days after the vulcanization.

(Test for Adhesion Stability)

A steel cord-rubber composite body of an unvulcanized state formed by coating steel cords with each of the rubber compositions is left to stand in a constant temperature and humidity chamber of 40° C. and 80% RH for 7 days and then vulcanized at 160° C. for 15 minutes to measure an initial adhesion as an indicator of the adhesion stability.

Comparative Example 1

A rubber composition is prepared according to the same compounding recipe as in the reference examples except that the composition according to the invention is not used as a test compound and the properties thereof are evaluated. The results are shown in Table 4.

Comparative Example 2

A rubber composition is prepared according to the same compounding recipe as in the reference examples except that 2 parts by mass of resorcin is compounded in the base rubber formulation as a test compound and the properties thereof are evaluated. The results are shown in Table 4.

Comparative Example 3

A rubber composition is prepared according to the same compounding recipe as in the reference examples except that 2 parts by mass of RF resin is compounded in the base rubber formulation as a test compound and the properties thereof are evaluated. The results are shown in Table 4. Moreover, the RF resin is prepared by the following method.

At first, 1100 g of water, 1100 g (10 mol) of resorcin and 1.72 g (10 mmol) of p-toluenesulfonic acid are charged into a four-necked flask equipped with a cooling tube, a stirrer, a thermometer, a dropping funnel and a tube for introduction of nitrogen, and then heated to 70° C. 477 g (5.9 mol) of a 37% formalin solution is added dropwise over 2 hours and the temperature is kept for 5 hours to complete the reaction. After the completion of the reaction, 4 g of an aqueous solution of 10% sodium hydroxide is added and neutralized, and thereafter the cooling device is substituted with a Dean-Stack type reflux condenser. Then, the temperature is raised to 150° C. while distilling off water, and further water is removed under a reduced pressure of 20 mmHg over 1 hour to obtain the RF resin. The thus obtained RF resin has a softening point of 124° C. and a residual resorcin content of 17%.

Comparative Example 4

A rubber composition is prepared according to the same compounding recipe as in the reference examples except that 2 parts by mass of a mixed polyester described in JP-A-7-118621 is compounded in the base rubber formulation as a test compound and the properties thereof are evaluated. The results are shown in Table 4. Moreover, the mixed polyester is prepared according to Example 1 of the above-described publication.

Into a 300 ml four-necked flask equipped with a reflux condenser and a thermometer are charged 108.9 g (0.99 mol) of resorcin, 131.4 g (0.90 mol) of adipic acid, 222.0 g (2.175 mol) of acetic anhydride and 0.54 g (0.5 wt % to resorcin) of pyridine, and the inside of the flask is purged with nitrogen, and then the mixture is stirred at room temperature for 15 minutes and heated to 100° C. and acetylated at this temperature for 2 hours. Thereafter, the system is heated while distilling off a by-product acetic acid from the system, and maturated at 140° C. for 1 hour and further at 240° C. for 2 hours. Then, the maturation is continued at 240° C. under a reduced pressure (50 mmHg). The resulting reaction mixture is discharged onto a porcelain dish to obtain 195.6 g of ocher candy-like body. The candy-like body is gradually crystallized by kneading with a glass rod. As a result of the analysis, the crystal contains 0.1 wt % of resorcin, 0.5 wt % of resorcin monoacetate and 0.8 wt % of resorcin diacetate. As a result of the measurement on the molecular weight through GPC, the weight-average molecular weight is about 30000 (conversion to PS).

TABLE 4

| | | | Referential Example 1 | Referential Example 2 | Referential Example 3 | Referential Example 4 | Referential Example 5 | Comparative Example 1 | Comparative Example 2 | Comparative Example 3 | Comparative Example 4 |
|---|---|---|---|---|---|---|---|---|---|---|---|
| Rubber Formulation | Natural Rubber | parts by mass | 100 | 100 | 100 | 100 | 100 | 100 | 100 | 100 | 100 |
| | Carbon Black (N326) | | 60 | 60 | 60 | 60 | 60 | 60 | 60 | 60 | 60 |
| | Sulfur | | 5 | 5 | 5 | 5 | 5 | 5 | 5 | 5 | 5 |
| | Zinc White | | 5 | 5 | 5 | 5 | 5 | 5 | 5 | 5 | 5 |
| | Vulcanization Accelerator[1] | | 1 | 1 | 1 | 1 | 1 | 1 | 1 | 1 | 1 |
| | Antioxidant[2] | | 2 | 2 | 2 | 2 | 2 | 2 | 2 | 2 | 2 |
| | Cobalt Compound[3] | | 1 | 1 | 1 | 1 | 1 | 1 | 1 | 1 | 1 |
| | Test Composition/Sort | | Example 1 | Example 2 | Example 3 | Example 4 | Example 5 | None | Resorcin | RF Resin | Polyester |
| | Compound Amount | | 2 | 2 | 2 | 2 | 2 | | 2 | 2 | 2 |
| Evaluation Result | Resistance to blooming | | ○ | ○ | ○ | ○ | ○ | ○ | X | Δ | ○ |
| | ML1 + 4(130° C.) | | 76.4 | 77.1 | 77.5 | 78.5 | 75.0 | 73.5 | 81.9 | 82.5 | 84.5 |
| | Initial adhesion | % | 100 | 100 | 100 | 100 | 100 | 100 | 100 | 100 | 100 |
| | Humidity-aged adhesion | % | 95 | 90 | 90 | 90 | 80 | 30 | 90 | 50 | 50 |
| | Adhesion stability | % | 100 | 100 | 100 | 100 | 100 | 100 | 70 | 75 | 100 |

[1] N,N'-dicyclohexyl-2-benzothiazyl sulfenamide [Manufactured by OUCHISHINKO CHEMICAL INDUSTRIAL CO., LTD., Trade name: NOCCELER DZ]
[2] N-phenyl-N'-1,3-dimethylbutyl-p-phenylenediamine [Manufactured by OUCHISHINKO CHEMICAL INDUSTRIAL CO., LTD., Trade name: NOCRAC 6C]
[3] Manufactured by OMG, Trade name: MANOBOND C22.5, Cobalt content = 22.5 mass %

The invention claimed is:

1. A compound represented by the following general formula (2):

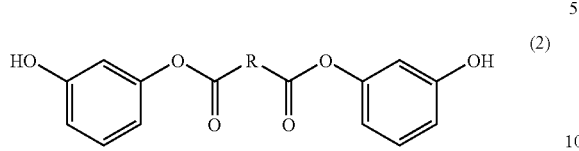
(2)

(wherein R represents a divalent aliphatic group having a carbon number of 1-16).

2. A compound according to claim 1, wherein R in the general formula (2) is an alkylene group having a carbon number of 2-10.

3. A compound according to claim 1, wherein R in the general formula (2) is ethylene group, butylene group or octylene group.

4. A composition comprising 60-100 wt % of the compound represented by the following general formula (2), 0-20 wt % of a compound represented by the following general formula (3) in which n is 2, 0-10 wt % of a compound represented by the following general formula (3) in which n is 3 and 0-10 wt % of a compound represented by the following general formula (3) in which n is 4-6:

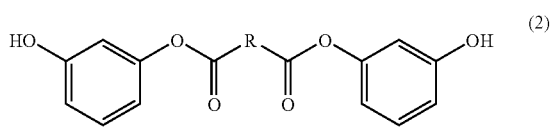
(2)

(where R represents a divalent aliphatic group having a carbon number of 1-16),

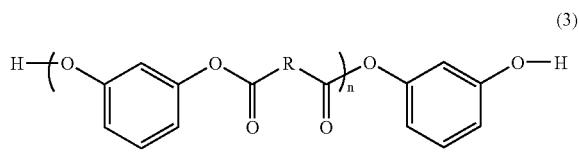
(3)

(wherein R is a divalent aliphatic group having a carbon number of 1-16, and n is an integer of 2-6).

5. A composition according to claim 4, wherein R in the general formula (2) and the general formula (3) is an alkylene group having a carbon number of 2-10.

6. A composition according to claim 4, wherein R in the general formula (2) and the general formula (3) is ethylene group, butylene group or octylene group.

* * * * *